(12) United States Patent
Crawford

(10) Patent No.: US 11,173,313 B2
(45) Date of Patent: Nov. 16, 2021

(54) IMPLANTABLE MEDICAL DEVICE WITH OFFLINE PROGRAMMING LIMITATIONS AND RELATED METHODS OF OPERATIONS

(71) Applicant: Advanced Neuromodulation Systems, Inc, Plano, TX (US)

(72) Inventor: Christopher S. L. Crawford, Sunnyvale, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 16/179,753

(22) Filed: Nov. 2, 2018

(65) Prior Publication Data
US 2020/0139142 A1 May 7, 2020

(51) Int. Cl.
*A61N 1/372* (2006.01)
*A61N 1/02* (2006.01)

(52) U.S. Cl.
CPC ..... *A61N 1/37276* (2013.01); *A61N 1/37217* (2013.01); *A61N 1/37258* (2013.01);
(Continued)

(58) Field of Classification Search
CPC A61N 1/372; A61N 1/37211; A61N 1/37252; A61N 1/37258; A61N 1/37264; A61N 1/37276; A61N 1/37282
See application file for complete search history.

(56) References Cited

U.S. PATENT DOCUMENTS 6,622,050 B2  9/2003 Thompson
6,880,085 B1  4/2005 Balczewski et al.
(Continued)

FOREIGN PATENT DOCUMENTS

EP  3466484 A1  4/2019

OTHER PUBLICATIONS

International Search Report for PCT/US2019/59485; dated Feb. 3, 2020; 8 pgs.
(Continued)

*Primary Examiner* — Allen Porter
(74) *Attorney, Agent, or Firm* — Norton Rose Fulbright US LLP

(57) ABSTRACT

In one embodiment, a method of programming an implantable medical device (IMD) to provide therapeutic operations for a patient, comprises: receiving first programming data by the IMD from the external programming device to provide therapeutic operations according to at least one instance of settings data during a first communication session; receiving second programming data by the IMD from the external programming device to define limitations of reprogramming during one or more subsequent offline programming sessions; conducting a second communication session between the IMD with an external programming device when network connectivity is not available; receiving third programming data by IMD from the external programming device to provide therapeutic operations according to at least one instance of settings data during the second communication session; and determining whether the third programming data is permitted according to limitations defined by the second programming data.

17 Claims, 11 Drawing Sheets

(52) U.S. Cl.
CPC .......... *A61N 1/37282* (2013.01); *A61N 1/025* (2013.01); *A61N 1/37247* (2013.01); *A61N 1/37254* (2017.08); *A61N 1/37264* (2013.01)

(56) References Cited

U.S. PATENT DOCUMENTS

| | | | |
|---|---|---|---|
| 7,027,872 | B2 | 4/2006 | Thompson |
| 7,039,810 | B1 | 5/2006 | Nichols |
| 7,155,290 | B2 | 12/2006 | Von Arx et al. |
| 7,228,182 | B2 | 6/2007 | Healy et al. |
| 7,475,245 | B1 | 1/2009 | Healy et al. |
| 7,664,553 | B2 | 2/2010 | Roberts |
| 7,801,611 | B2 | 9/2010 | Persen et al. |
| 7,818,067 | B2 | 10/2010 | Healy et al. |
| 7,831,828 | B2 | 11/2010 | Von Arx et al. |
| 7,890,180 | B2 | 2/2011 | Quiles |
| 7,930,543 | B2 | 4/2011 | Corndorf |
| 7,940,933 | B2 | 5/2011 | Corndorf |
| 8,102,999 | B2 | 1/2012 | Corndorf |
| 8,218,445 | B2 | 7/2012 | Katz et al. |
| 8,331,563 | B2 | 12/2012 | Healy et al. |
| 8,649,757 | B2 | 2/2014 | Roberts et al. |
| 8,682,437 | B2 | 3/2014 | Kalpin et al. |
| 9,401,894 | B2 | 7/2016 | Kalpin et al. |
| 9,722,803 | B1 | 8/2017 | Ellingson et al. |
| 9,942,051 | B1 | 4/2018 | Poltorak |
| 9,974,108 | B2 | 5/2018 | Polefko |
| 10,147,502 | B2 | 12/2018 | Paffel et al. |
| 10,306,472 | B2 | 5/2019 | Battiwalla et al. |
| 10,493,287 | B2 | 12/2019 | Yoder et al. |
| 10,554,632 | B2 | 2/2020 | Lange |
| 10,576,290 | B2 | 3/2020 | Schilling et al. |
| 10,599,814 | B2 | 3/2020 | Landrum et al. |
| 2003/0083719 | A1* | 5/2003 | Shankar .............. A61N 1/37211 607/60 |
| 2003/0088295 | A1* | 5/2003 | Cox .................. A61N 1/37282 607/60 |
| 2003/0093127 | A1* | 5/2003 | Dalal ................. A61N 1/37282 607/32 |
| 2005/0033369 | A1 | 2/2005 | Badelt |
| 2005/0261934 | A1 | 11/2005 | Thompson |
| 2005/0283210 | A1 | 12/2005 | Blischak et al. |
| 2005/0288736 | A1 | 12/2005 | Persen et al. |
| 2006/0265022 | A1* | 11/2006 | John ....................... A61B 5/02 607/45 |
| 2007/0016257 | A1 | 1/2007 | Brown et al. |
| 2007/0150013 | A1 | 6/2007 | Ding et al. |
| 2008/0140163 | A1 | 6/2008 | Keacher et al. |
| 2008/0163361 | A1 | 7/2008 | Davis et al. |
| 2008/0288029 | A1 | 11/2008 | Healy et al. |
| 2009/0048644 | A1 | 2/2009 | Stahmann et al. |
| 2009/0281598 | A1 | 12/2009 | Haubrich et al. |
| 2010/0066500 | A1 | 3/2010 | Ljungstrom et al. |
| 2011/0145588 | A1 | 6/2011 | Stubbs et al. |
| 2011/0172740 | A1 | 7/2011 | Matos |
| 2012/0197347 | A1 | 8/2012 | Olson et al. |
| 2014/0055230 | A1 | 2/2014 | Hoyme et al. |
| 2014/0185805 | A1 | 7/2014 | Andersen |
| 2014/0273824 | A1 | 9/2014 | Fenner et al. |
| 2015/0033365 | A1 | 1/2015 | Mellor et al. |
| 2015/0089590 | A1* | 3/2015 | Krishnan ................ H04L 63/08 726/3 |
| 2015/0117645 | A1* | 4/2015 | Carlson ............... H04L 63/0435 380/262 |
| 2015/0281285 | A1 | 10/2015 | Bharali et al. |
| 2016/0330573 | A1 | 11/2016 | Masoud et al. |
| 2016/0342762 | A1 | 11/2016 | Goetz |
| 2017/0259072 | A1 | 9/2017 | Newham et al. |
| 2017/0296076 | A1* | 10/2017 | Mahajan ............ A61B 5/02405 |
| 2018/0028827 | A1 | 2/2018 | Schilling et al. |
| 2018/0241564 | A1 | 8/2018 | Peterson |
| 2018/0243573 | A1 | 8/2018 | Yoder et al. |
| 2018/0309766 | A1 | 10/2018 | Marnfeldt |

OTHER PUBLICATIONS

International Search Report for PCT/US2019/59489; dated Feb. 4, 2020; 9 pgs.
International Search Report for PCT/US2019/59497; dated Feb. 4, 2020; 9 pgs.
International Search Report for PCT/US2019/59501; dated Feb. 4, 2020; 14 pgs.
International Search Report for PCT/US2019/59507; dated Feb. 6, 2020; 8 pgs.
Epstein, M. A. et al. "Security for the Digital Information Age of Medicine: Issues, Applications, and Implementation," Journal of Digital Imaging, vol. 11, No. 1, Feb. 1998, 12 pages.
Chan et al., "On the Distribution and Revocation of Cryptographic Keys in Sensor Networks," IEEE Transactions on Dependable and Secure Computing, vol. 2, Issue 3, Jul.-Sep. 2005, pp. 233-247 (Year: 2005); 15 pages.
Halperin, Daniel, et al. "Security and Privacy for Implantable Medical Devices," IEEE Pervasive Computing vol. 7, No. 1 (2008): 11 pages.

* cited by examiner

IMPLANTABLE MEDICAL DEVICE WITH OFFLINE PROGRAMMING LIMITATIONS AND RELATED METHODS OF OPERATIONS

Implantable medical devices have changed how medical care is provided to patients with a number of chronic illnesses and disorders. For example, implantable cardiac devices improve cardiac function in patients with heart disease by improving quality of life and reducing morality rates. Respective types of implantable neurostimulators provide a reduction in pain for chronic pain patients and reduce motor difficulties in patients with Parkinson's disease and other movement disorders. A variety of other medical devices are proposed and are in development to treat other disorders in a wide range of patients.

Many implantable medical devices and other personal medical devices are programmed by a physician or other clinician to optimize the therapy provided by a respective device to an individual patient. For some implantable device legacy designs, the programming occurs using inductive wireless telemetry. An external coil is placed on a given patient's body to inductively couple to a coil in the device implanted within the patient's body. The program values or parameters are communicated over the telemetry connection. Since the inductive coupling requires dose immediate contact, there is a very small likelihood of a third party establishing a communication session with the patient's implanted device without the patient's knowledge.

More recent implantable devices employ wireless telemetry over greater distances using radio frequency protocols. For example, selected implantable medical devices employ low energy BLUETOOTH® to communicate programming data between an external programmer device and a respective implanted device. Certain mechanisms are implemented to provide a degree of security for the communication of data between the external and implanted devices.

Also, a number of device management, home care, or remote care networks (collectively referred to herein as device management system) have been developed or proposed to allow remote access to physiological and other data stored by implanted devices of patients and possibly to reprogram operations of the implanted devices of patients in certain circumstances.

Although the adoption of longer range telemetry capabilities and remote care networks provides a number of clinical benefits to patient care, there is some risk of malicious parties inappropriately accessing patient data and/or effecting the medical therapy provided by implanted or other personal medical devices.

SUMMARY

Figure 1:
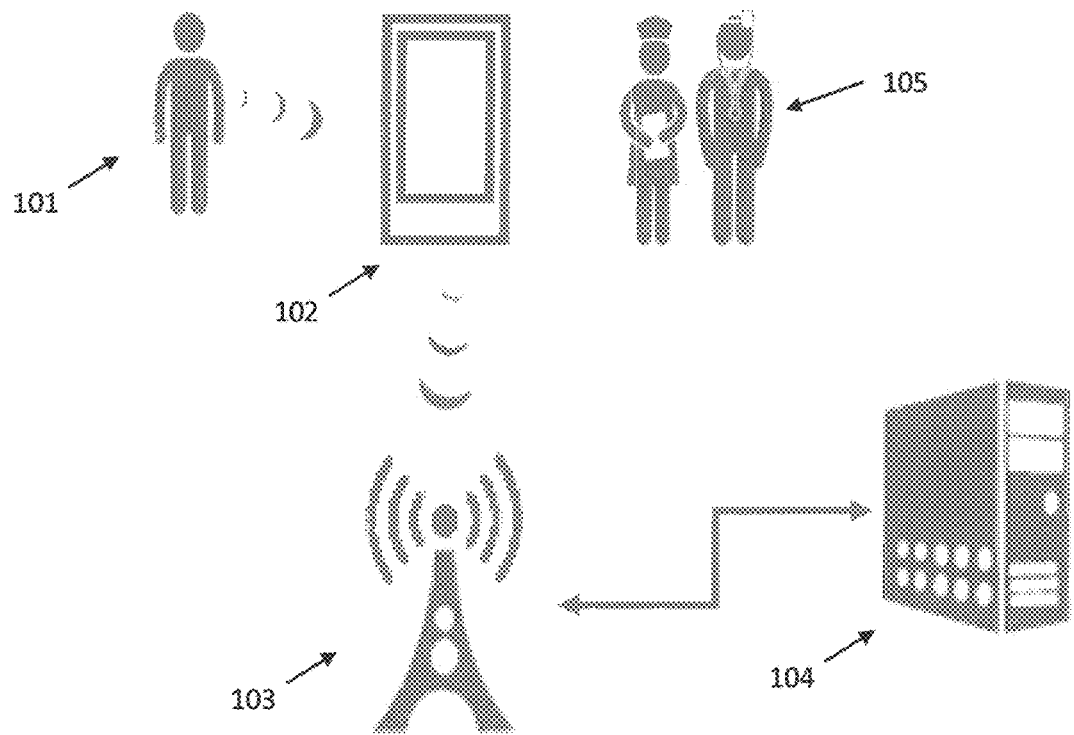
FIG. 1 depicts a system in which an implanted medical device is programmed according to some representative embodiments.

In certain embodiments, an implantable medical device (IMD) is adapted to conduct operations according to programming data defined by one or more clinicians. The IMD verifies the validity of the programming data using validation data before conducting device operations according to the programming data. The IMD is adapted to communicate with one or more patient controller devices and/or clinician programmer devices. The patient controller devices and/or clinician programmer devices may in turn communicate with a device management system. The programming data may be signed by one or more keys to assist the verification operations. The validation data may be generated by a device management system. The validation data may be generated by a clinician programmer.

In some embodiments, the IMD is selected from the list consisting of: a neurostimulation device, a cardiac rhythm management device, an implantable drug delivery pump, and an insulin dispensing device.

In some embodiments, a method of programming an implantable medical device (IMD) to provide therapeutic operations for a patient, comprises: conducting a first communication session between the IMD with an external programming device when network connectivity for a remote server for medical device management is not available for the external programming device; receiving programming data by the IMD from the external programming device to provide therapeutic operations according to at least one instance of settings data during the first communication session, wherein the at least one instance of settings data is validated by a temporary key; conducting a second communication session between the IMD with an external device when network connectivity to the remote server for medical device management is available for the external device; receiving validation data for the at least one instance of settings data that is signed with a key corresponding to the IMD; processing the received validation data to verify the received validation data against a key of the IMD; and replacing validation data signed using the temporary key with the received validation data. The method may also comprise conducting therapeutic operations according to the at least one instance of settings data to provide a therapy to the patient after determining that the at least one instance of settings data is verified.

In some embodiments, the temporary key corresponds to a clinician or clinician device. In some embodiments, the IMD stores a collection of temporary keys and the IMD searches the collection for a matching key for validation data signed with a temporary key during verification operations. In some embodiments, the external device that has network access is a patient controller device adapted to communicate with the IMD. In some embodiments, the external device that has network access is a clinician programmer device adapted to communicate with the IMD. In some embodiments, the IMD causes a respective instance of settings data that is validated by a temporary key to become invalid after a defined period of time passes without replacement by validation data signed with a key corresponding to the IMD. In some embodiments, the IMD reverts to one or more default therapeutic settings upon invalidation of the respective instance of settings data.

In some embodiments, a clinician programmer device for programming an implantable medical device (IMD) comprises: a processor for executing instructions to control the clinician programmer device; wireless communication circuitry for communicating with the IMD and for communicating with a remote server for medical device management; and memory for storing data and executable instructions, wherein the executable comprises code for causing the processor to (1) provide one or more user interface (UI) screens to interact with a clinician to define therapeutic settings for the IMD, (2) validate the therapeutic settings with the remote server when network connectivity is obtained by obtaining validation data from the remote server that is signed with a key corresponding to the IMD, (3) create validation data that is signed with a temporary key when network connectivity to the remote server is not available, and (4) communicate the therapeutic settings and validation data to the IMD to control therapeutic operations of the IMD.

In some embodiments, the executable instructions of the clinician programmer device comprise code to cause the processor to (a) query the IMD to identify prior therapeutic settings with validation data signed with a temporary key, (b) communicate with the remote server when network connectivity is available to validate the prior therapeutic settings by obtaining updated validation data signed with a key corresponding to the IMD, and (c) communicate the updated validation data to the IMD. The communication circuitry of the clinician programmer device may comprise a first and second set of communication circuitry for providing at least two different wireless communication protocols.

In some embodiments, an implantable medical device (IMD) comprises: therapeutic circuity for controlling delivery of a medical therapy to a patient; a processor for controlling the IMD according to executable code; wireless communication circuitry for conducting wireless communications; and memory for storing data and executable code, wherein the executable comprises code for causing the processor to (1) communicate with an external programming device to define therapeutic settings for operation of the IMD, (2) perform validation operations on one or more instances of therapeutic settings by determining whether a respective instance of therapeutic settings is accompanied by validation data signed with a key corresponding to the IMO or by a temporary key, and (3) replace instances of validation data signed with a temporary key upon a subsequent communication session with an external device that has network access to a remote server for remote medical device management operations. In some embodiments, the memory of the IMD stores a collection of temporary keys and the processor searches the collection for a matching key for validation data signed with a temporary key.

In some embodiments, a method for operating a system for management of implantable medical devices (IMDs), comprises: conducting communication sessions with a plurality of clinician programmer devices while the clinician programmer devices are engaged in respective programming sessions with IMDs; signing first validation data for first programming data with keys corresponding to respective IMDs; communicating the first signed validation data to corresponding clinician programmers for communication to respective IMDs to cause the IMDs to conduct therapeutic operations according to programming data validated by respective instances of validation data; receiving and storing second programming data from a plurality of clinician programmer devices, wherein the second programming data was created during programming sessions with IMDs without network connectivity to the system for management of IMDs; conducting communication sessions with patient controller devices for a plurality of IMDs that were programmed with the second programming data; reconciling programming of the plurality of IMDs that were programmed with the second programming data with data stored by the system for management of IMDs; generating second validation data for instances of the second programming data with keys corresponding to respective IMDs; and communicating the second signed validation data to cause IMDs to conduct therapeutic operations according to programming data validated by respective instances of second validation data.

In some embodiments, an implantable medical device (IMD) comprises: therapeutic circuitry for controlling delivery of a medical therapy to a patient; a processor for controlling the IMD according to executable code; wireless communication circuitry for conducting wireless communications; and memory for storing data and executable code, wherein the executable comprises code for causing the processor to (1) communicate with an external programming device to define therapeutic settings for operation of the IMD, (2) perform validation operations on one or more instances of therapeutic settings by determining whether a respective instance of therapeutic settings is accompanied by permanent validation data or temporary validation data, wherein the validation operations comprise analyzing temporary validation data against at least one key of a plurality of cryptographic keys stored by the IMD, and (3) communicate with an external programming device or patient controller device according to a revocation protocol for receipt of available revocation data from a remote device management system, wherein the revocation data identifies one or more cryptographical keys of the plurality of cryptographic keys that are no longer trusted.

In some embodiments, a method for operating a system for management of implantable medical devices (IMDs), comprises: conducting communications sessions with a plurality of clinician programmer devices, wherein some of the communication sessions occur while the plurality of clinician programmer devices are engaged in respective programming sessions with IMDs and wherein the communication sessions with the plurality of clinician programmer devices include communication of data pertaining to offline programming of IMDs; conducting communications sessions with a plurality of patient controller devices, wherein the communication sessions with the patient controller devices include communication of data pertaining to offline programming of IMDs; reconciling programming session data received from the plurality of clinician programmer devices with programming session data received from patient controller devices to identify instances of unauthorized IMD programming; and distributing revocation data to patient controller devices to be downloaded to corresponding IMDs, wherein the revocation data identifies cryptographic keys that are no longer trusted.

In some embodiments, the method further comprises: identifying a legitimate clinician programmer device that uses a cryptographic key to be revoked; replacing the cryptographic key on the legitimate clinician programmer device during a communication session with the respective clinician programmer device.

In some embodiments, a method of programming an implantable medical device (IMD) to provide therapeutic operations for a patient, comprises: conducting a first communication session between the IMD with an external programming device; receiving first programming data by the IMD from the external programming device to provide therapeutic operations according to at least one instance of settings data during the first communication session; receiving second programming data by the IMD from the external programming device to define limitations of reprogramming during offline programming sessions; conducting a second communication session between the IMD with an external programming device when network connectivity with a remote server of a medical device management is not available for the external programming device; receiving third programming data by IMD from the external programming device to provide therapeutic operations according to at least one instance of settings data during the second communication session; determining whether the third programming data is permitted according to limitations defined by the second programming data; and conducting therapeutic operations by the IMD according to the third programming data after determining that the third programming data is permitted.

In some embodiments, an implantable medical device (IMD) comprises: therapeutic circuitry for controlling delivery of a medical therapy to a patient; a processor for controlling the IMD according to executable code; wireless communication circuitry for conducting wireless communications; and memory for storing data and executable code, wherein the executable comprises code for causing the processor to (1) communicate with a respective external programming device to define therapeutic settings for operation of the device while the respective external programming device is in online or offline communication states with a device management system, (2) communicate with an external programming device to define offline programming limitations, (3) perform validation operations on one or more instances of therapeutic settings by determining whether a respective instance of therapeutic settings is accompanied by validation data, and (4) determine whether a respective instance of therapeutic settings is consistent with previously communicated limitations for offline programming if the respective instance of therapeutic settings is not accompanied by validation data from the device management system.

DETAILED DESCRIPTION

FIG. 1 depicts a system in which an implanted medical device is programmed according to some representative embodiments. The implanted medical device (not shown in FIG. 1) is implanted within patient 101. Examples of suitable implantable medical devices include neurostimulators such as the Protege™, Prodigy™, Proclaim™, Infinity™ pulse generators available from Abbott (Plano Tex). Also, other example implantable medical devices include cardiac rhythm management devices and cardiac devices include Ellipse™ implantable Cardioverter/Defibrillator (ICDs), Fortify Assura™ ICDs, Assurity MRI™ pacemakers, and Endurity™ pacemakers available from Abbott (Sylmar, Calif). Any suitable implantable medical device or personal medical device may operate according to embodiments described herein.

At appropriate times, the implanted medical device of patient 101 communicates with clinician programmer device 102 which is operated by one or more clinicians 105. The programming clinician 105 utilizes one or more user interface screens of device 102 to define or control a therapy provided to patient 101 by the implanted medical device. The clinician(s) may define or set one or more therapy parameters. For example, the clinician may define pulse amplitudes, pulse frequencies, pulse patterns, pacing delays, and/or a variety of other therapy parameters depending upon the implanted device and the intended therapy for patient 101. Examples of programming parameters for neurostimulation devices may be found in (1) Parameters of Spinal Cord Stimulation and Their Role in Electrical Charge Delivery: A Review, Neuromodulation. 2016 June; 19(4):373-84, Miller et al.; (2) Novel Spinal Cord Stimulation Parameters in Patients with Predominant Back Pain, Neuromodulation 2013; 16: 370-375, Jeffrey Tiede et al.; (3) Are 10 kHz Stimulation and Burst Stimulation Fundamentally the Same? Neuromodulation 2017; 20: 650-653, Dirk De Ridder et al. An example of programming methodology for cardiac rhythm management devices may be found in insights From a Cardiac Resynchronization Optimization Clinic as Part of a Heart Failure Disease Management Program, Journal of the American College of Cardiology, Volume 53, Issue 9, March 2009, Wilfried Mullens et al.

During a programming session, programming data is communicated from clinician programmer device 102 to one or more remote device management servers 104 via network 103. The set of programming data is subjected to authorization and validation processes to ensure that only programming data from authorized clinicians will accepted by the implanted medical device of patient 101. Suitable security algorithms may be employed to validate and authorize communication between clinician programmer device 102 and servers 104, such as communication of user/clinician identifiers, passwords, device identifiers, network identifiers, security/cryptographic keys, digital certificates, location data, and/or the like. Also, this application discloses novel security algorithms for validation, authorization, and other security related operations for programming data for respective embodiments.

Conventional security algorithms may be applied to assist portions of the communication of programming data and/or other patient data according to some embodiments. Conventional information technology products use "Identification" protocols to provide user identity (in the form of a user ID) to one or more relevant security systems. A given security system will typically search through all the security objects that it manages to identify the specific identity corresponding to the data supplied from a respective user.

The fact that the user claims to be represented by a specific identity object (identified by its user ID) does not necessarily mean that this is true. To ascertain that an actual user can be mapped to a specific abstract user object in the system, and therefore be granted user rights and permissions specific to the abstract user object, the user must provide evidence to prove his identity to the system. Authentication is the process of ascertaining claimed user identity by verifying user-provided evidence. A respective instance of evidence provided by a user in the process of user authentication is called a credential. Different systems may require different types of credentials to ascertain user identity and may even require more than one credential. In computer systems, the credential very often takes the form of a user password, which is a secret known only to the individual and the system. Credentials may take other forms, however, including PIN numbers, certificates, tickets, etc.

Authorization is the process of determining whether an already identified and authenticated user is allowed to access information resources in a specific way. Authorization is often the responsibility of the service providing access to a resource, Access control lists are frequently employed to manage authorization operations.

A discussion of conventional security protocols may be found in "Cloud computing security requirements: A systematic review," 2012 Sixth International Conference on Research Challenges in Information Science (RCS), Valencia, 2012, pp. 1-7. (doi: 10.1109/RCIS.2012.6240421) which is incorporated herein by reference. A further example of a known user identification and authentication system for cloud applications is described in U.S. Pat. No. 9,172,605 which is incorporated herein by reference.

Servers 104 may also assist in validation and creation of the programming data. For example, servers 104 may compare the programming data submitted by a clinician for review by one or more automated validation processes created to optimize therapies based on previously determined clinical data. If there is a discrepancy or a possible improvement, servers 104 may communicate suggested changes to the clinician(s) operating device 102. Also, servers 104 may offer application services to assist the programming process. For example, servers 104 may serve user interface screens using a suitable protocol (e.g., HTML) to device 102 to permit the clinician(s) to define the therapy for patient 101.

When the given set of programming data is suitably defined, server(s) 104 generate data to permit the programming data to control the therapeutic operations of the implanted medical device of patient 101. Specifically, if server(s) 104 determine that clinician programmer 104 is being operated by a properly identified clinician with proper programming permissions, server(s) 104 may generate authorization/validation data to accompany the programming data. Server(s) 104 communicate the authorization/validation data to clinician programming device 102 via network 103. Clinician programming device 102 communicates the programming data and the authorization/validation data to the implanted medical device of patient 101. The implanted medical device of patient 101 analyzes the authorization/validation data. If the authorization/validation data is determined by the implanted medical device to be valid, the implanted medical device conducts therapy operations (e.g., generating electrical pulses for application to tissue of the patient, delivery of pharmaceuticals, and/or the like) according to the programming data.

As used herein, validation data is data that provides information to ascertain the integrity of the programming data and/or whether the programming data was generated by a properly authorized clinician or other user. Validation data may be generated by generating a value from therapeutic settings and/or programming metadata using a checksum, digest, or other suitable function. The function may include application of one or more cryptographic keys or the result of the function may be varied by application of one or more cryptographic keys. The respective keys used for cryptographic processing may include keys selected according to public-key cryptography or asymmetric cryptography (e.g., RSA (Rivest-Shamir-Adleman) cryptography and Elliptic Curve Cryptography (ECC)). Additional details regarding generation of the validation data is discussed herein.

Figure 2:
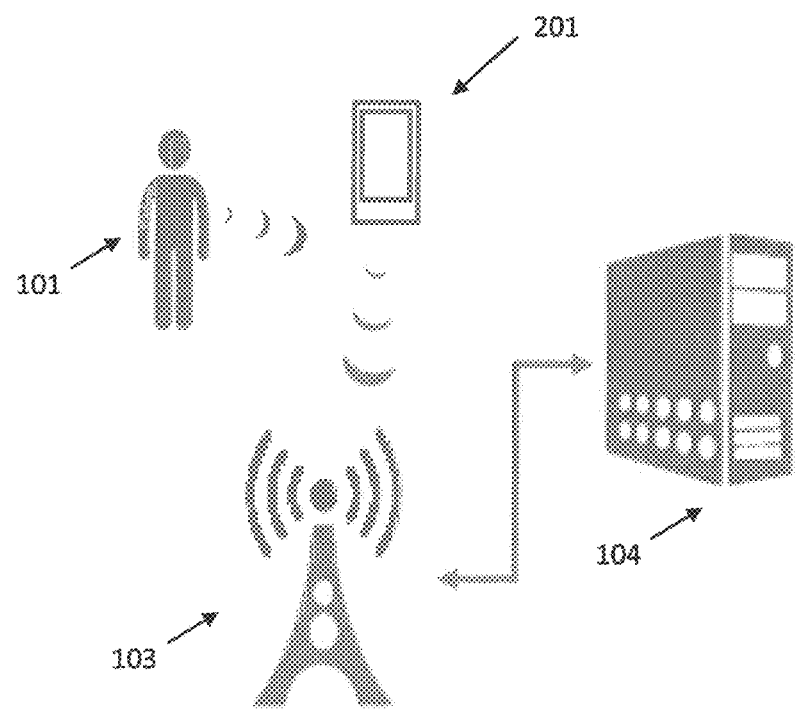
FIG. 2 depicts a system in which an implanted medical device communicates with patient controller device which, in turn, communicates with one or more remote device management servers.

FIG. 2 depicts a system in which an implanted medical device communicates with patient controller device 201 which, in turn, communicates with one or more remote device management servers 104. Patient 101 may utilize patient controller device 201 for one or more of a variety of tasks. For example, patient 101 may interact with patient controller device 201 to check the status of the patient's implanted medical device (battery level, current operating mode, etc.). Also, the implanted medical device may monitor physiological signal or processes of the patient. Patient controller device 201 may communicate with the implanted medical device to access stored physiological data. The patient controller device 201 may display a suitable indication of the patient's condition (e.g., heart rate, glucose level, neurological activity, etc.). The accessed physiological or other patient data may be communicated to one or more servers 104. The physiological data may be analyzed to monitor the patient's condition. For example, the physiological data may be analyzed to identify if the patient is experiencing undesired cardiac conditions such as episodes of tachycardia, arrhythmias, and other conditions. Automated processing may occur to Identify relevant medical conditions, Alerts to the patient 101 or to the patient's medical professions may be given by patient controller 201 and/or server(s) 104 if warranted by the physiological data.

Also, depending upon the implanted medical device, patient 101 may Interact with patient controller device 201 to control some aspects of the patient's therapy. For example, neurostimulation devices frequently include multiple stimulation programs. Depending upon the patient's experience of pain at any given time, the patient may switch between available programs to select the program that provides the most suitable pain relief. Also, patient controller device 201 may enable patient 101 to control stimulation amplitude (for certain neurostimulation devices). Patient 101 may enter relevant information via one or more user interface screens to control stimulation. For example, the implanted medical device may employ different therapy settings when the patient is asleep or when the patient is active. The patient may provide suitable input to switch between these therapy settings at times desired by the patient. Alternatively, the implanted medical device may modify operations depending upon the intake or ingestion of pharmaceutical agents by patient 101. The patient may enter relevant information via patient controller device 201 to indicate such events. The controller device 201 may communicate the information to the implanted medical device which controls its operations according to the communicated information.

As previously discussed, the implanted medical device may validate therapy parameters downloaded to the device before conducting therapeutic operations according to the values.

Although operating a device management system to provide validation data reduces the probability of a malicious third party from programming implantable medical devices (IMDs) without authorization, network connectivity is required to permit the communication with one or more servers of the device management system. In certain environments or occasions, network connectivity may not be possible for a clinician. For example, many health care facilities do not provide consistent network access in all locations. If an implantable medical device management system is implemented where immediate network connectivity is required, clinicians would have significant burdens to complete required medical protocols for medical device management operations.

Some embodiments provide a multi-stage programming methodology that does not require network connectivity for all operations of device programming. In some embodiments, IMDs and clinician programmers are adapted to permit device programming in an offline mode (i.e., without an available network connection to a server of a device management system). Offline programming is followed up by subsequent connection to the device management system by patient controller devices and/or clinician programmer devices. In subsequent communication sessions, validation data can be downloaded to IMDs to manage the integrity and security of programming data of the IMDs.

In some representative embodiments, patient IMDs and clinician programmers include functionality to limit or reduce the probability of a malicious individual from exploiting the offline programming to provide unauthorized programming for patient IMDs. In certain embodiments, a clinician programmer will generate temporary validation data that is signed with a cryptographic key assigned to the clinician programmer and/or the clinician. A respective IMD will check the temporary validation data against an internal store of cryptographical keys before conducting therapeutic operations according to the programming data. A malicious individual will need to duplicate the functionality of the clinician programmer and compromise a secret key before being able to exploit the offline programming mode.

Although the use of cryptographic keys decreases the probability of an individual user from conducting unauthorized device programming, cryptographic keys can become compromised. For example, certain cryptographic key pairs have been shown to be computationally identified much more quickly and with fewer processing resources than theoretical limits. In some embodiments, IMDs are adapted to communicate through clinician programmer devices and/or patient controller devices with the device management system to obtain revocation data. The revocation data may identify one or more cryptographic keys that are no longer trusted. Accordingly, if a malicious individual is detected using a compromised key, future programming sessions using the cryptographic key may be blocked.

In other embodiments, revocation data may revoke the validity of specific instances of programming data. For example, the device management system may be used to audit programming data and programming metadata to identify specific instances of unauthorized programming. Identified unauthorized programming data may be reversed in addition to revoking future use of the compromised cryptographic key(s).

Figure 3A:
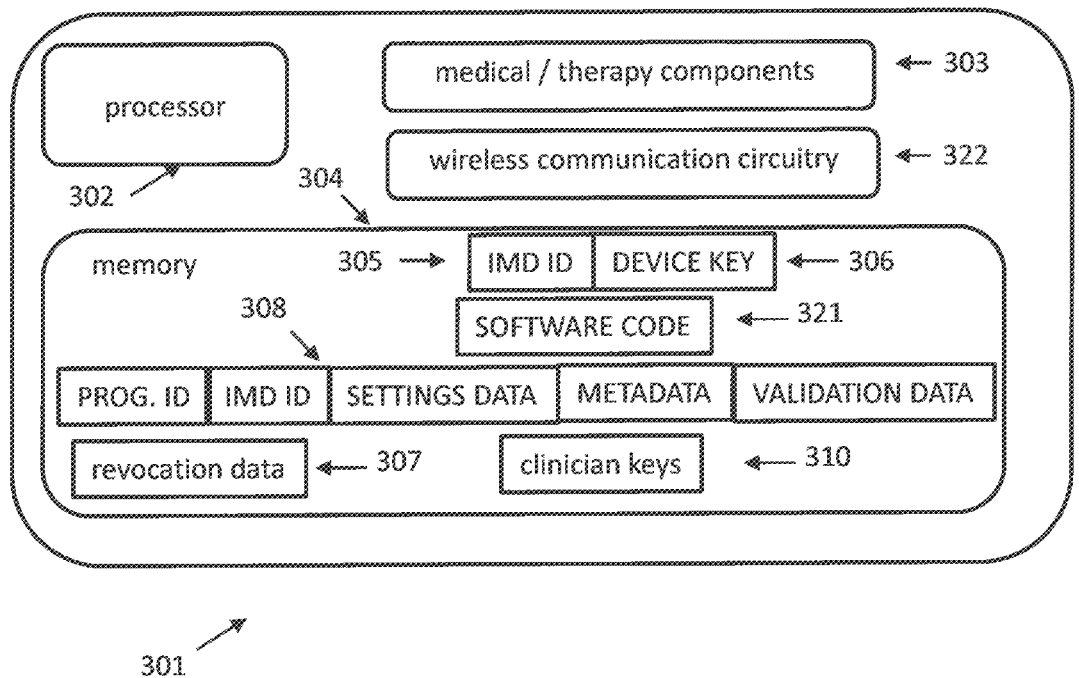
FIG. 3A depicts an implantable or personal medical device according to some embodiments.
Figure 3B:
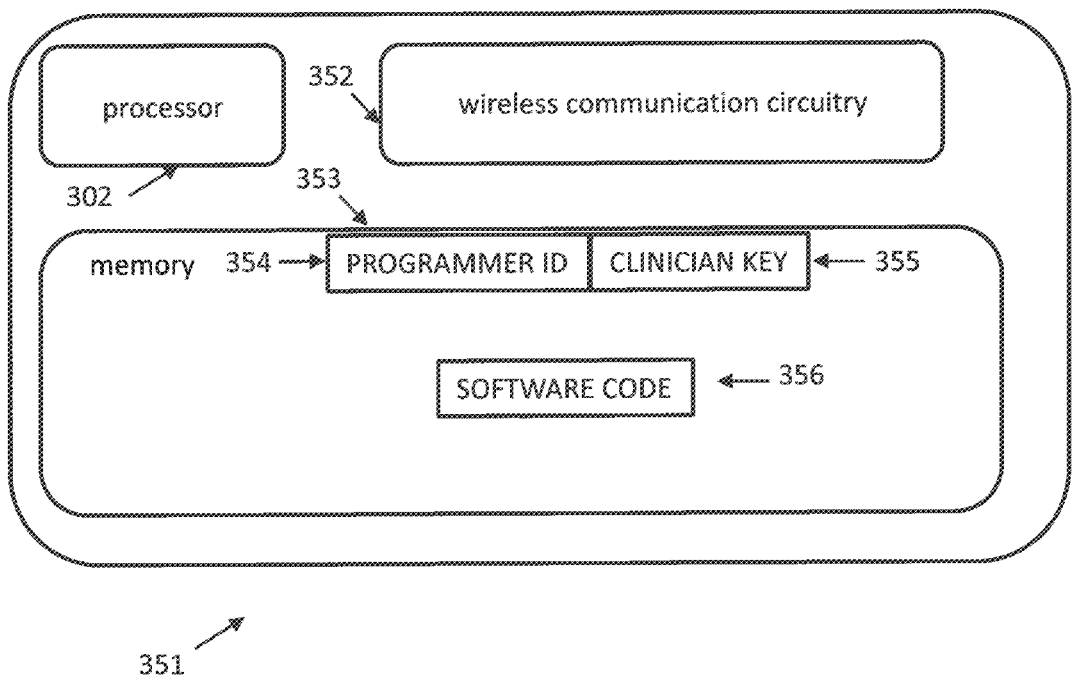
FIG. 3B depicts a clinician programmer device according to some embodiments.

FIG. 3A depicts implantable or personal medical device 301 according to some embodiments. Medical device 301 includes wireless communication circuitry 322 to conduct communication sessions with clinician programmer 351 (shown in FIG. 3B) after implantation, Wireless communication circuitry 352 may support communications using one or more communication protocols including inductive communication protocols and/or the lower energy BLUETOOTH® protocol as examples.

Clinician programmer 351 includes processor 302, memory 353, and wireless communication circuitry 352. Memory 363 stores relevant data and software code 356 to control operations of programmer 351. Memory 353 may store an identifier (e.g., a serial number) of programmer 351 for use during programming sessions. Also, memory 353 may store clinician key 355 for use during programming session as discussed herein. Wireless communication circuitry 352 may include complementary circuitry to conduct communications according to the protocol(s) implemented by medical device 301. Wireless communication circuitry 352 may also include additional wireless communication capabilities such as circuitry for 802.11 protocols ("Wi-Fi") for network communication with one or more servers of a device management system. Wireless communication circuitry 352 may also include wireless telephony network communication capabilities.

Medical device 301 includes one or more processors or controllers 302 to control device operations. Medical device 301 includes medical or therapy components 303 to provide the therapy to the patient and/or to monitor or measure one or more physiological conditions of the patient. Medical device 301 includes memory 304 to store executable instructions and data. The data may include a device identifier 305 and one or more device keys 306. For example, device key 306 may store one of a pair of asymmetric encryption keys with the other key stored by server 104. The pair of keys for a given device 301 may be used to securely create and employ validation data according to some embodiments. Although the present disclosure refers to device key 306, the specific key selected for a given device need not necessarily be unique. The same key may be assigned to one or more devices (whether implantable medical devices, clinician programmers, and/or patient controller devices). Although device identifier 305 is shown as stored in memory 304, device identifier 305 may be retained elsewhere in device 301. For example, many device components (e.g., processors, integrated circuits, wireless communication circuitry, etc.) include identifiers that are hard-encoded in the components and are readily retrievable. The identifiers of the subcomponents may be used as the medical device identifier in lieu of a value stored in conventional memory of device 301 according to some embodiments. Memory 304 further stores software code 321 to control operations of device 301. Software code 321 includes code to implement operations discussed herein.

Device 301 includes one or more instances of programming data 308 in memory 304 that defines how device 301 conducts therapeutic or medical operations according to some embodiments. In some embodiments, each instance of programming data 308 includes a program identifier. Also, each instance of programming data 308 includes a field for device identifier data. The device identifier data in programming data 308 is compared against the device identifier 305 to ensure that the programming data 308 is intended for use by the specific device 301.

Each instance of programming data 308 may include settings data (the various device parameters) that define the therapeutic or medical operations to be provided by device 301. For example, for a neurostimulation device for chronic pain, the settings data may include an electrode configuration for delivery of electrical pulses, a stimulation pattern identifier (tonic stimulation, burst stimulation, noise stimulation, and/or the like), pulse parameters, one or more frequency parameters, cycling parameters, timing parameters, and/or the like.

Each instance of programming data 308 is accompanied with its respective metadata. The metadata may include relevant data that is not directly used by device 301 to control specific device operations. For example, the metadata may include data that identifies the physician or clinician that created or programmed the settings data. The metadata may include an identifier of the clinician programmer device that was used to create the settings data, the date of creation, the data of last modification, the physical location where programming occurred, and/or any other relevant data.

Each instance of programming data 308 includes validation data. The validation data is used by device 301 to ensure that the settings data is intended for device 301 and is properly authorized to control operations of device 301. In some embodiments, validation data is created using a checksum algorithm, a cryptographic hash function, and/or similar suitable processing. For example, the other data in programming data 308 may be represented by characters in respective strings. Each character in sequence is applied to the applicable hash function or suitable function to generate an output hash value or similar value. Known checksum functions apply exclusive-OR (XOR) and/or modular sum operations in succession to each character or value in a sequence of characters or values. The UNIX command "cksum" provides a well-known implementation of checksum operations as one example.

The checksum value or other relevant data may be encrypted with a suitable cryptographical key (e.g., the corresponding key of the key pair used for device 301). The encrypted data is then stored in device 301 as the validation data in some embodiments.

When device 301 attempts to verify the validity of an instance of programming data 308, device 301 recalculates the checksum value or relevant data using the same methodology used to create the original validation data in the instance of programming data 308 and generates local comparison data. Device 301 then decrypts the encrypted data of the validation data using its device key 306. Device 301 compares the decrypted data against the local comparison data. If the two sets of data match, the settings data is valid and device 301 continues with its operations according to the settings data (assuming that there is no applicable data in revocation data 307 to indicate otherwise as discussed herein for some embodiments).

As previously discussed, a cryptographic hash algorithm may be employed for validation data operations according to some embodiments such as the SHA-1 (Secure Hash Algorithm 1) and SHA-2 (Secure Hash Algorithm 2) as examples.

Under ordinary circumstances, device 301 is programmed by one or more clinicians and the programming data is signed using a private encryption key of device 301 by server 104. Since server 104 is remote from the clinician(s) and device 301, a network connection is necessary to facilitate the programming workflow. However, network connectivity is not always available at the time of programming. In many institutional facilities, network connectivity in an operating room or other clinical setting can be intermittent or non-existent. A programming methodology that requires network connectivity as a condition to create or test therapeutic operations can be quite problematic for clinicians and patients.

In some embodiments, an implantable medical device or personal medical device is adapted to conduct programming operations with and without network connectivity while maintaining flexibility to provide authorization and validation operations to programming data.

Figure 4:
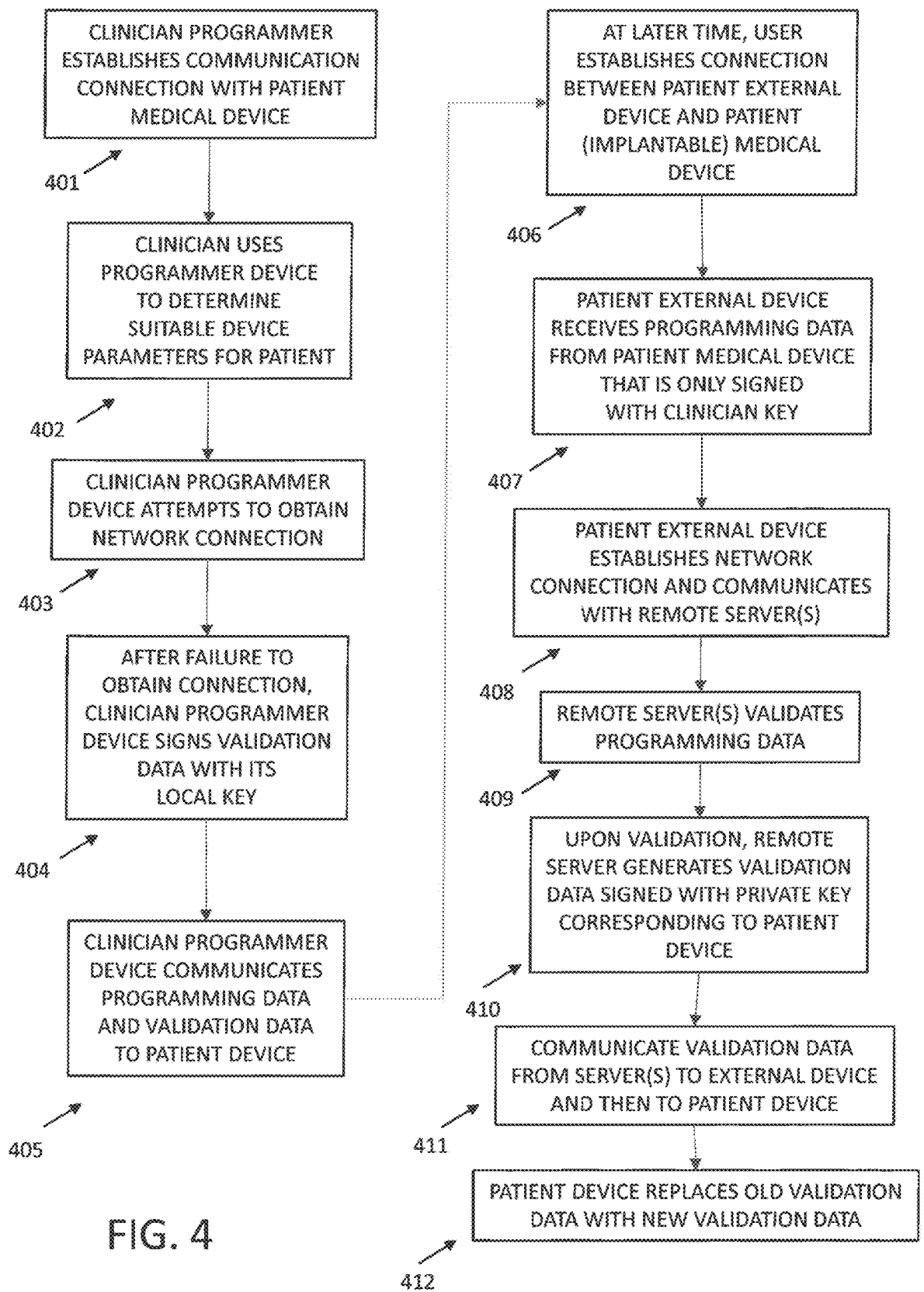
FIG. 4 depicts a programming work flow according to some embodiments where network connectivity is not available during an initial programming session.

FIG. 4 depicts a programming work flow according to some embodiments where network connectivity is not available during an initial programming session.

In 401, a clinician uses a clinician programmer device to establish a communication connection between the clinician programmer and an implantable or personal medical device of the patient. The communication connection may be established using suitable communication methods such as inductive wireless communication, low energy BLUETOOTH® communication, and medical band wireless communication as examples. An example of BLUETOOTH® communication between an implantable medical device and a programmer device is found in U.S. Pat. No. 9,894,691, which is incorporated herein by reference.

In 402, the clinician uses the clinician programmer device to determine suitable device and/or therapy parameters for the patient. For example, the clinician may employ a neurostimulation programming methodology to identify suitable stimulation parameters to address chronic pain of the patient using the St. Jude Medical™ Clinician Programmer App with BurstDR™ Stimulation executing on an iOS™ iPhone or iPad device (Apple Corp.). Any suitable medical device programming may occur including programming of cardiac rhythm management therapies, deep brain stimulation therapies, cortical stimulation therapies, dorsal root ganglion stimulation therapies, and insulin, drug, pharmaceutical, or biologic delivery therapies, as examples.

In 403, the clinician programmer device attempts to establish a network connection with one or more server(s) 104. For this workflow, it is assumed that the network connection is not available. For example, the clinician location may interfere with or block network connectivity. After the network connection fails, the clinician programmer signs the validation data with its local key (404). In some embodiments, the clinician programmer calculates the checksum data and encrypts the data with its local key. Any suitable key signing operations may be applied. In 405, the clinician programmer device communicates programming data and validation data to the patient device. The patient device may then provide operations according to the programming data after completing the processing the programming data and validation data as discussed herein.

At a later time, the user/patient establishes a connection between a patient external device and the patient (implantable) medical device (406). In 407, the patient external device receives programming data from patient medical device that is only signed with a clinician key. In 408, the patient external device establishes a network connection and communicates with remote server(s) 104. In 409, the remote server 104 validates programming data. In 410, upon proper validation, the remote server 104 generates validation data signed with private key corresponding to patient device 301. When the validation process determines that the programming data is improper, further operations are discussed below. In 411, upon successful validation, the validation data is communicated from the server 104 to external device and then to patient device. In 412, the implantable or personal medical device replaces the old validation data (signed with the clinician key) with the new validation data (signed with the private key corresponding to the medical device 301).

Figure 5:
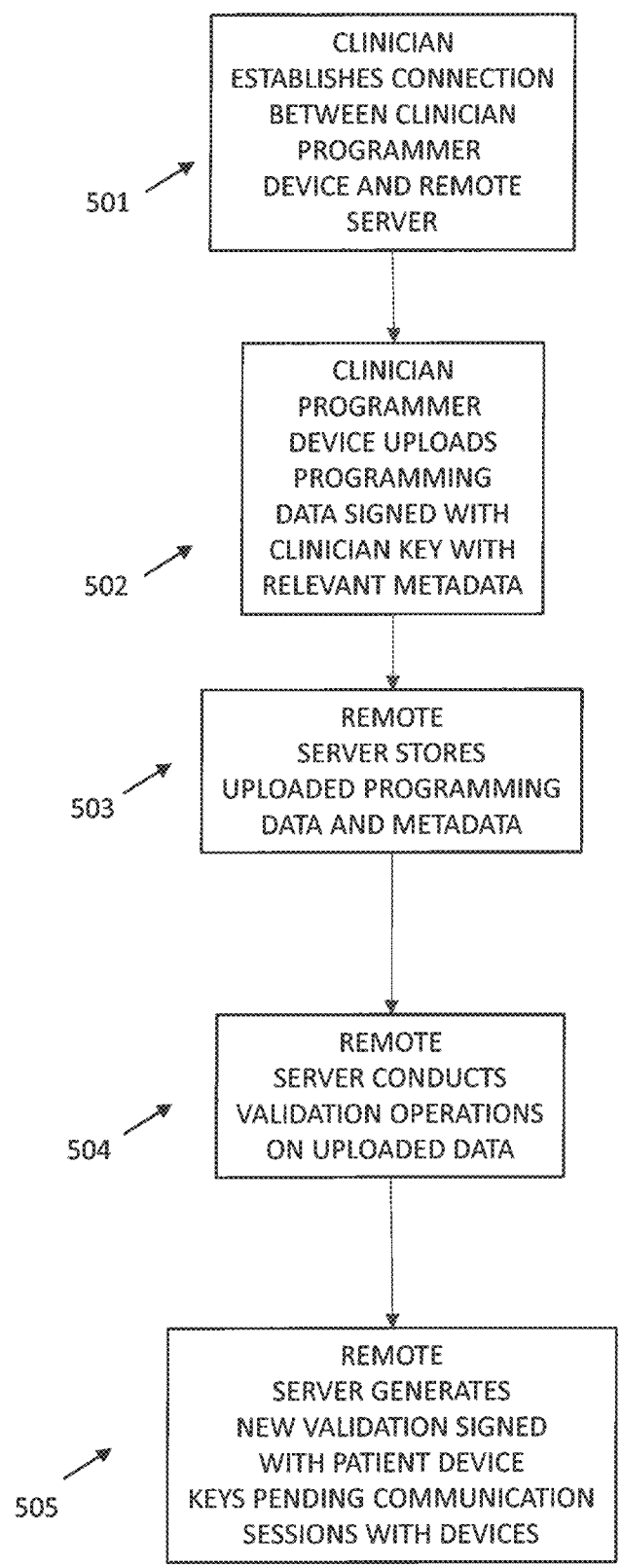
FIG. 5 describes operations performed after a clinician has performed non-networked programming sessions according to some embodiments.

FIG. 5 depicts programming data validation operations according to some embodiments. As previously discussed, certain programming operations may occur between a clinician programmer device and patient medical devices without using network connectivity between the clinician programmer and one or more remote servers. FIG. 5 describes operations performed after a clinician has performed such non-networked programming sessions.

In 501, the clinician establishes a connection between clinician programmer device and remote server. The establishment of the communication connection may involve one or more known network security processes including the use of user identifiers, passwords, key exchanges, network location analysis, and/or the like to validate the identity of the clinician and/or the clinician device.

In 502, the clinician programmer device uploads programming data signed with clinician key with relevant metadata for the non-networked programming sessions. The metadata may include relevant data such as patient identifier (s), patient device identifier(s), programming session time and date, the physical location of a programming session, and/or the like. In 503, the remote server stores uploaded programming data and metadata. In 504, the remote server conducts validation operations on uploaded data. In 505, the remote server generates new validation signed with patient device keys pending communication sessions with devices. The new validation may be communicated to patient devices upon subsequent connections with the patient devices to the one or more remote servers (see 406-412 in FIG. 4). The patient controller devices then, in turn, communicate the new (permanent) validation data to the respective IMDs of the patients.

Figure 6:
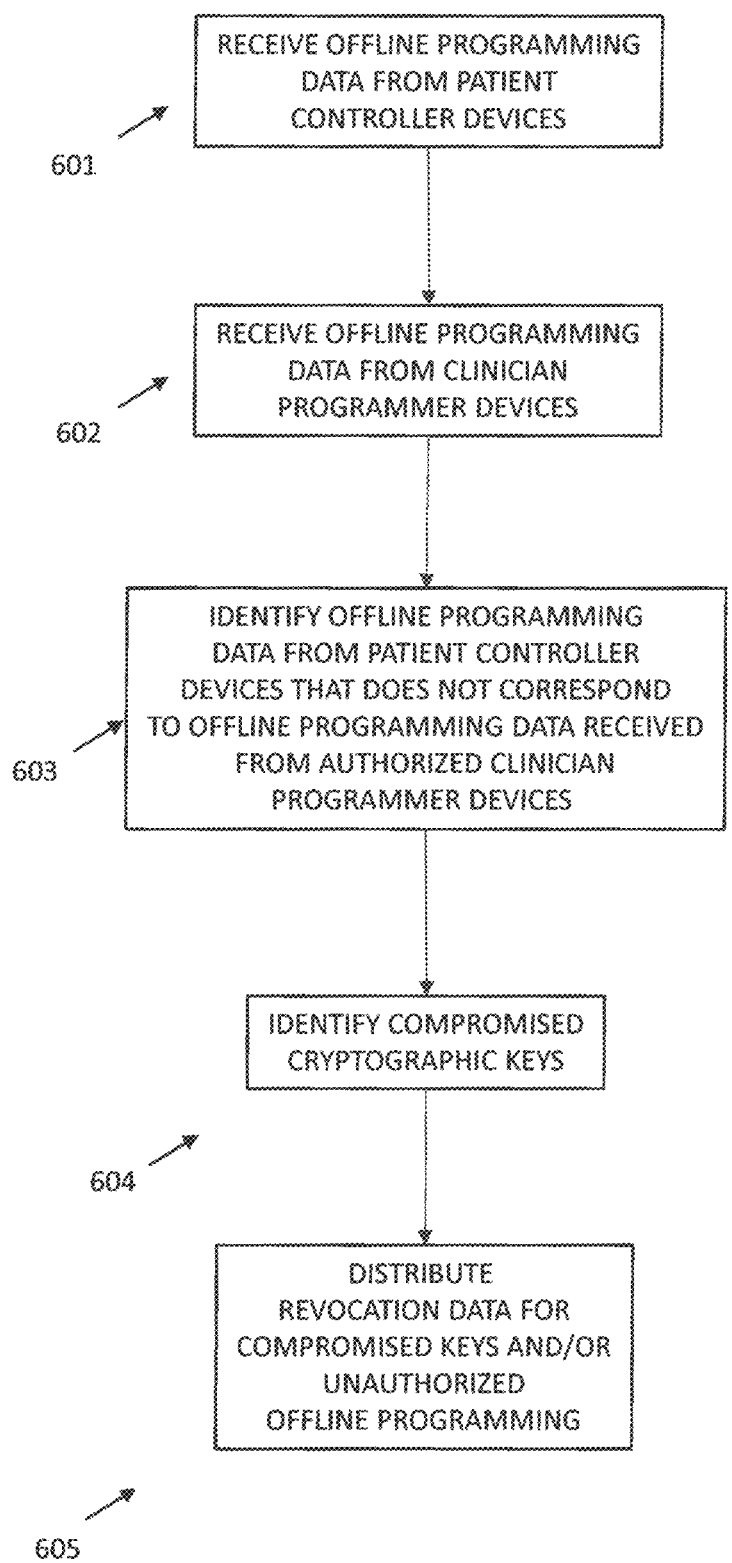
FIG. 6 depicts programming data analysis operations according to some embodiments to detect and remediate instances of unauthorized programming.

In describing some embodiments herein, it has been assumed that the programming of IMDs in an offline mode has occurred in an authorized manner. Although the management of cryptographic keys and use of the keys for validation operations increases the security of the programming process, it is possible that one or more cryptographic keys may be compromised for unauthorized use. FIG. 6 depicts programming data analysis operations according to some embodiments to detect and remediate instances of unauthorized programming.

In 601, offline programming data is received from patient controller devices. For example, a given patient may return home after the patient's IMD was programmed in an offline manner at a doctor's office at a health care facility. The patient may check the status of the patient's implant and retrieve physiological data for display on the patient's patient controller device. When performing these operations, the patient controller may employ a network connection at the patient's residence to connect to a remote care/device management system. The patient controller device then automatically uploads the programming data (therapeutic settings and/or programming metadata) to the device management system.

In 602, offline programming data is received from clinician programmer devices. After online programming sessions occur, the respective clinicians may return their devices to a suitable (e.g., centralized) location for their offices. The clinician programmers may be connected to a wired network (e.g., an office ethernet local area network) or other network. When connected, the clinician programmers then automatically upload the programming data (therapeutic settings and/or programming metadata) to the device management system.

In 603, the device management system identifies offline programming data from patient controller devices that does not correspond to offline programming data received from authorized clinician programmer devices. Reconciliation between the programming data received from patient controller devices and clinician programmer devices occur. When a given clinician programmer device connects with the device management system, the clinician programmer device is authenticated using transmission of clinician identifiers and credentials and other appropriate security operations. The authenticated clinician programmer may provide a list of all programming sessions performed since the last time that the clinician programmer connected with the device management system. The device management system will then possess a record of valid offline programming sessions. If the device management system has a record of an offline programming session with programming data identifying the respective clinician programmer as received from a patient controller device but the properly authenticated clinician programmer does not report the programming session, it is likely that unauthorized programming has occurred.

Other reconciliations operations may be applied. For example, analysis of programming data may reveal that two clinician programming devices conducted programming sessions in disparate geographical locations in a similar time frame. Identification of such programming sessions may indicate that a clinician programming device has been cloned.

In 604, one or more compromised cryptographic keys are identified. The cryptographic key for a given clinician and/or clinician device that was used in an authorized programming session is identified using the programming session metadata. In 605, revocation data for compromised keys and/or unauthorized offline programming is distributed. The revocation data may cause IMDs to automatically delete or otherwise render invalid any programming data identified to be unauthorized. Also, the revocation of now untrusted cryptographic keys will prevent future unauthorized offline programming sessions for IMDs associated with patient devices connecting to the device management system and receiving the download of revocation data.

Figure 7:
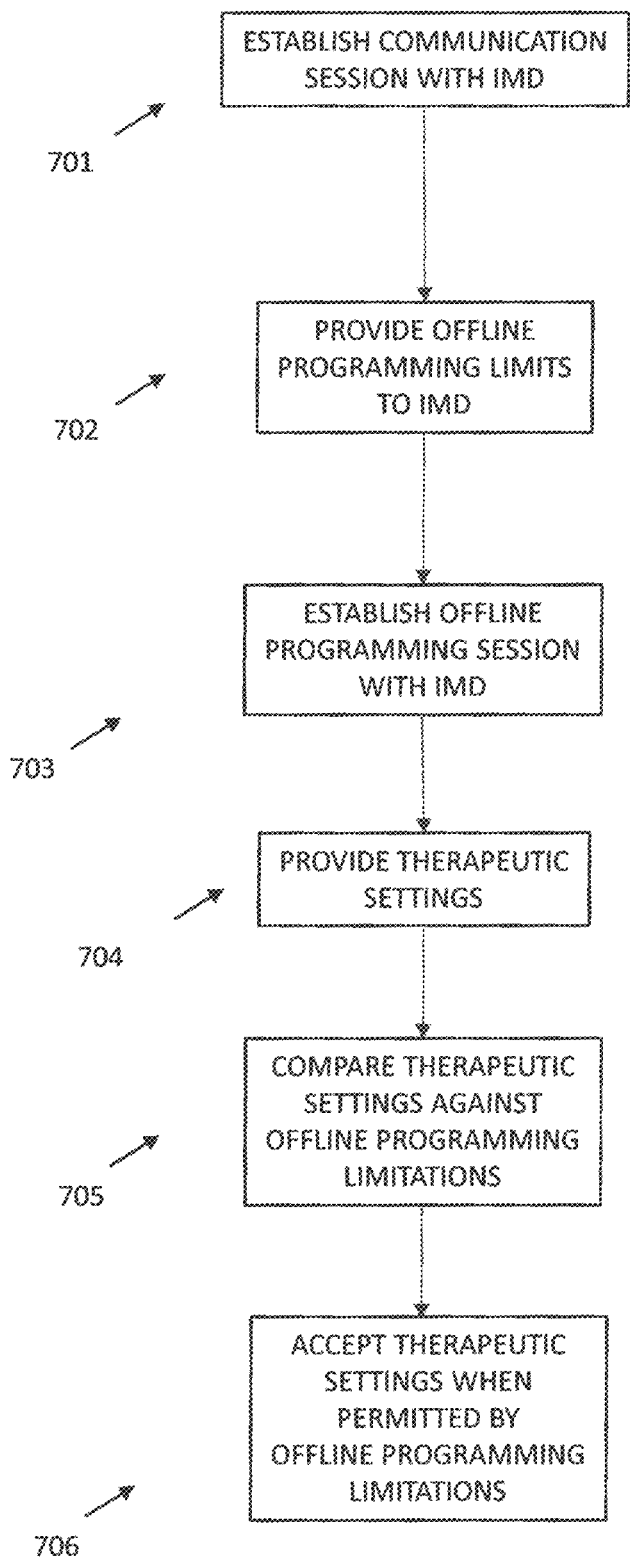
FIG. 7 depicts programming data validation operations for offline programming according to some embodiments.

FIG. 7 depicts programming data validation operations for offline programming according to some embodiments.

In 701, a communication session is established with an IMD by a clinician programming device. In 702, the clinician programming device provides offline programming limits to IMD. The offline programming limitations control the changes to therapeutic settings that may be applied in an offline mode. For example, the clinician may determine that certain electrodes of a deep brain stimulation system cause undesired side effects on the patient due to their location proximate to relevant neural tissue. The clinician may provide limitations that prevent therapeutic settings from using such electrodes when programmed in an offline mode. Similarly, the clinician may identify certain cardiac rhythm therapies or cardiac therapy settings that are possibly unsuitable for a given patient. The clinician may prevent use of such therapies or settings by defining suitable limitations.

In 703, a clinician programmer establishes an offline programming session with IMD at a later time. In 704, the clinician programmer provides new or modified therapeutic settings to the IMD. In 705, the IMD compares the new or modified therapeutic settings against the previously defined offline programming limitations. In 706, the IMD accepts the new or modified therapeutic settings when permitted by offline programming limitations. If the changes are not permitted, the IMD may signal to the clinician programmer that the changes are not accepted (not shown) and a network connection to the device management system is necessary to program beyond the defined limitations.

As discussed herein, some embodiments may be employed for operations related to programming implantable medical devices such as neurostimulation devices, cardiac rhythm management devices, glucose monitoring devices, and medical agent infusion devices as examples.

Figure 8:
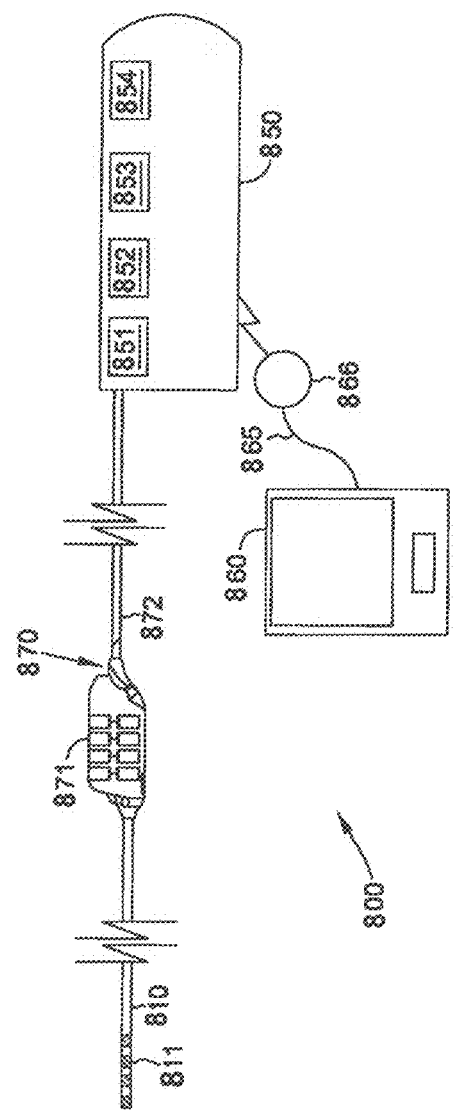
FIG. 8 depicts a neurostimulation system adapted according to embodiments disclosed herein.

FIG. 8 depicts a neurostimulation system that may be employed according to some embodiments. Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue of the spinal cord for the purpose of chronic pain control. While a precise understanding of the interaction between the applied electrical energy and the nervous tissue is not fully appreciated, it is known that application of an electrical field to spinal nervous tissue can effectively inhibit certain types of pain transmitted from regions of the body associated with the stimulated nerve tissue to the brain. Under certain stimulation conditions, applying electrical energy to the spinal cord associated with regions of the body afflicted with chronic pain can induce "paresthesia" (a subjective sensation of numbness or tingling) in the afflicted bodily regions. Certain stimulation patterns (such as BurstDR™ stimulation provided by pulse generators of Abbott) modulate neural activity to reduce chronic pain without inducing paresthesia.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord. The stimulation leads are then tunneled to another location within the patients body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

Stimulation system 800 generates electrical pulses for application to tissue of a patient, or subject, according to one embodiment. Stimulation system 800 includes an implantable pulse generator (IPG) 850 that is adapted to generate electrical pulses for application to tissue of a patient. Implantable pulse generator 850 typically includes a metallic housing that encloses a controller 851, pulse generating circuitry 852, a battery 853, far-field and/or near field communication circuitry 854, and other appropriate circuitry and components of the device. Controller 851 typically includes a microcontroller or other suitable processor for controlling the various other components of the device. Software code is typically stored in memory of implantable puke generator 850 for execution by the microcontroller or processor to control the various components of the device. The software code stored in memory of puke generator 850 may support operations of embodiments disclosed herein.

Implantable puke generator 850 may comprise one or more attached extension components 870 or be connected to one or more separate extension components 870. Alternatively, one or more stimulation leads 810 may be connected directly to implantable puke generator 850. Within implantable puke generator 850, electrical pukes are generated by puke generating circuitry 852 and are provided to switching circuitry. The switching circuit connects to output wires, traces, lines, or the like (not shown) which are, in turn, electrically coupled to internal conductive wires (not shown) of a lead body 872 of extension component 870. The conductive wires, in turn, are electrically coupled to electrical connectors (e.g., "Bal-Seal" connectors) within connector portion 871 of extension component 870. The terminals of one or more stimulation leads 810 are inserted within connector portion 871 for electrical connection with respective connectors. Thereby, the pulses originating from implantable pulse generator 850 and conducted through the conductors of lead body 872 are provided to stimulation lead 810. The pulses are then conducted through the conductors of stimulation lead 810 and applied to tissue of a patient via electrodes 811. Any suitable known or later developed design may be employed for connector portion 871.

For implementation of the components within implantable pulse generator 850, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 850. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 810 may include a lead body of insulative material about a plurality of conductors within the material that extend from a proximal end of stimulation lead 810 to its distal end. The conductors electrically couple a plurality of electrodes 811 to a plurality of terminals (not shown) of stimulation lead 810. The terminals are adapted to receive electrical pulses and the electrodes 811 are adapted to apply stimulation pulses to tissue of the patient. Also, sensing of physiological signals may occur through electrodes 811, the conductors, and the terminals. Additionally or alternatively, various sensors (not shown) may be located near the distal end of stimulation lead 810 and electrically coupled to terminals through conductors within the lead body 872. Stimulation lead 810 may include any suitable number of electrodes 811, terminals, and internal conductors.

Figure 9A:
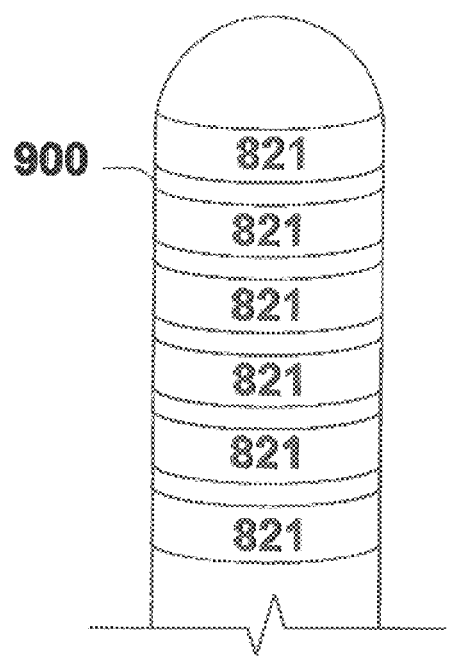
FIGS. 9A-9C depict portions of stimulation leads that may be used in the neurostimulation system of FIG. 8.
Figure 9B:
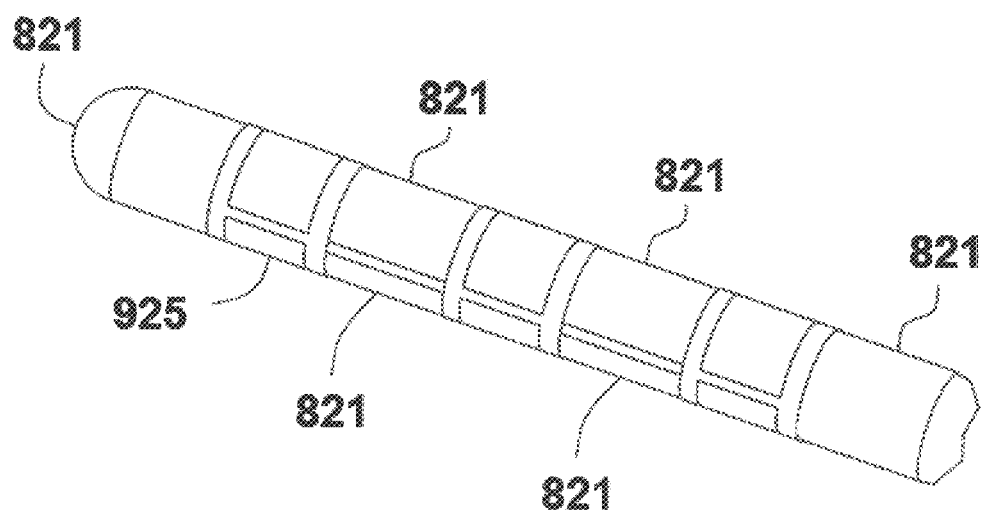
Figure 9C:
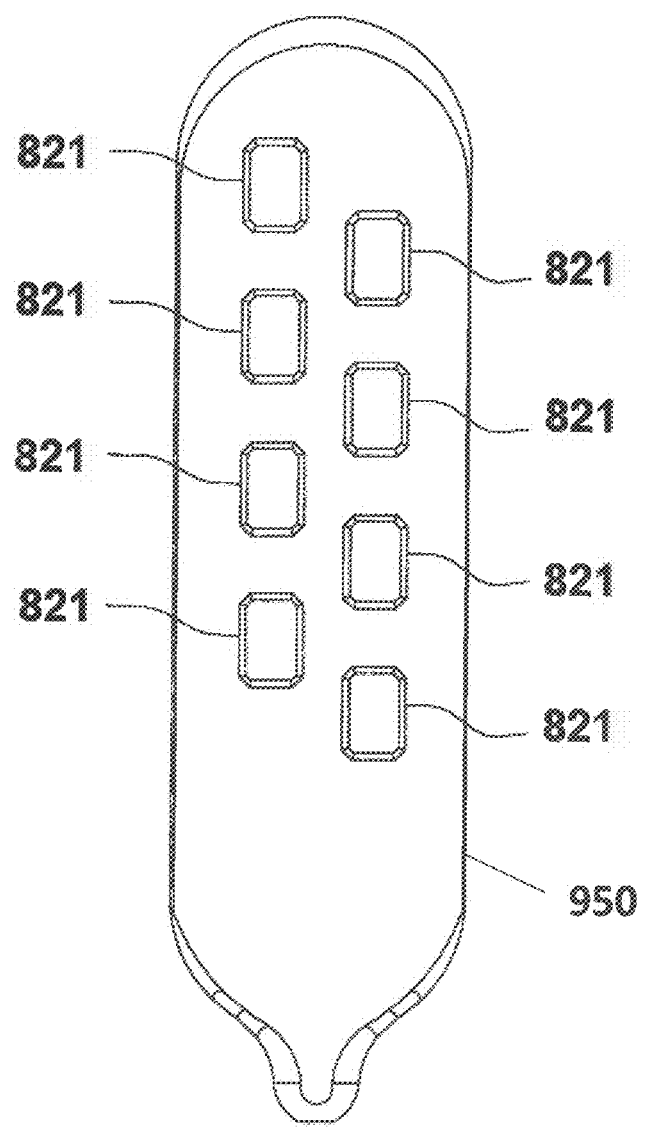

FIGS. 9A-9C respectively depict stimulation portions 900, 925, and 950 for inclusion at the distal end of stimulation lead 110. Stimulation portions 900, 925, and 950 each include one or more electrodes 821. Stimulation portion 900 depicts a conventional stimulation portion of a "percutaneous" lead with multiple ring electrodes. Stimulation portion 925 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference. Stimulation portion 950 includes multiple planar electrodes on a paddle structure.

Controller device 860 (shown in FIG. 8) may be implemented to recharge battery 853 of implantable pulse generator 850 (although a separate recharging device could alternatively be employed). A "wand" 865 may be electrically connected to controller device 860 through suitable electrical connectors (not shown). The electrical connectors are electrically connected to a "primary" coil 866 at the distal end of wand 865 through respective wires (not shown). Typically, primary coil 866 is connected to the wires through capacitors (not shown). Also, in some embodiments, wand 865 may comprise one or more temperature sensors for use during charging operations.

The patient then places the primary coil 866 against the patient's body immediately above the secondary coil (not shown), i.e., the coil of the implantable medical device. Preferably, the primary coil 866 and the secondary coil are aligned in a coaxial manner by the patient for efficiency of the coupling between the primary and secondary coils. Controller device 860 generates an AC-signal to drive current through primary coil 866 of wand 865. Assuming that primary coil 866 and secondary coil are suitably positioned relative to each other, the secondary coil is disposed within the field generated by the current driven through primary coil 866. Current is then induced in secondary coil. The current induced in the coil of the implantable pulse generator is rectified and regulated to recharge battery of implantable puke generator 850. The charging circuitry may also communicate status messages to controller device 860 during charging operations using pulse-loading or any other suitable technique. For example, controller device 860 may communicate the coupling status, charging status, charge completion status, etc.

External controller device 860 is also a device that permits the operations of implantable puke generator 850 to be controlled by user after implantable puke generator 850 is implanted within a patient, although in alternative embodiments separate devices are employed for charging and programming. Also, multiple controller devices may be provided for different types of users (e.g., the patient or a clinician). Controller device 860 can be implemented by utilizing a suitable handheld processor-based system that possesses wireless communication capabilities. Software is typically stored in memory of controller device 860 to control the various operations of controller device 860. The software code stored in memory of device 860 may support the operations according to embodiments disclosed herein. Also, the wireless communication functionality of controller device 860 can be integrated within the handheld device package or provided as a separate attachable device. The user interface functionality of controller device 860 is implemented using suitable software code for interacting with the user and using the wireless communication capabilities to conduct communications with implantable pulse generator 850.

Controller device 860 preferably provides one or more user interfaces to allow the user to operate implantable pulse generator 850 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 850 modifies its internal parameters in response to the control signals from controller device 860 to vary the stimulation characteristics of stimulation pulses transmitted through stimulation lead 810 to the tissue of the patient. Neurostimulation systems, stimsets, and multi-stimset programs are discussed in PCT Publication No. WO 2001/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Pulse generator device 850 and controller device 860 may be adapted to apply different types of neurostimulation. One or more stimulation sets or programs may be defined with tonic stimulation. Also, these devices may support burst stimulation as disclosed in U.S. Pat. No. 8,934,981 which is incorporated herein by reference. In burst stimulation, groups of pulses are provided at a relatively high frequency (greater than 250 Hz) with adjacent groups of pulses separated by a quiet period. The groups are repeated at a relatively lower frequency (e.g., 40 Hz or other physiologically relevant frequencies). These devices may support "noise" stimulation such as described in U.S. Pat. No. 9,498,634, which is incorporated herein by references. These devices may also support high frequency stimulation (e.g., 1500 Hz-20,000 Hz).

Example commercially available neurostimulation systems include the PROTEGE™, PRODIGY™, PROCLAIM™, INFINITY™ pulse generators and CLINICIAN PROGRAMMER APP from Abbott Laboratories. Example commercially available stimulation leads include the QUATTRODE™, OCTRODE™, AXXESS™, LAMITRODE™, TRIPOLE™, EXCLAIM™, PENTA™, and INFINITY™ stimulation leads from Abbott Laboratories.

Figure 10:
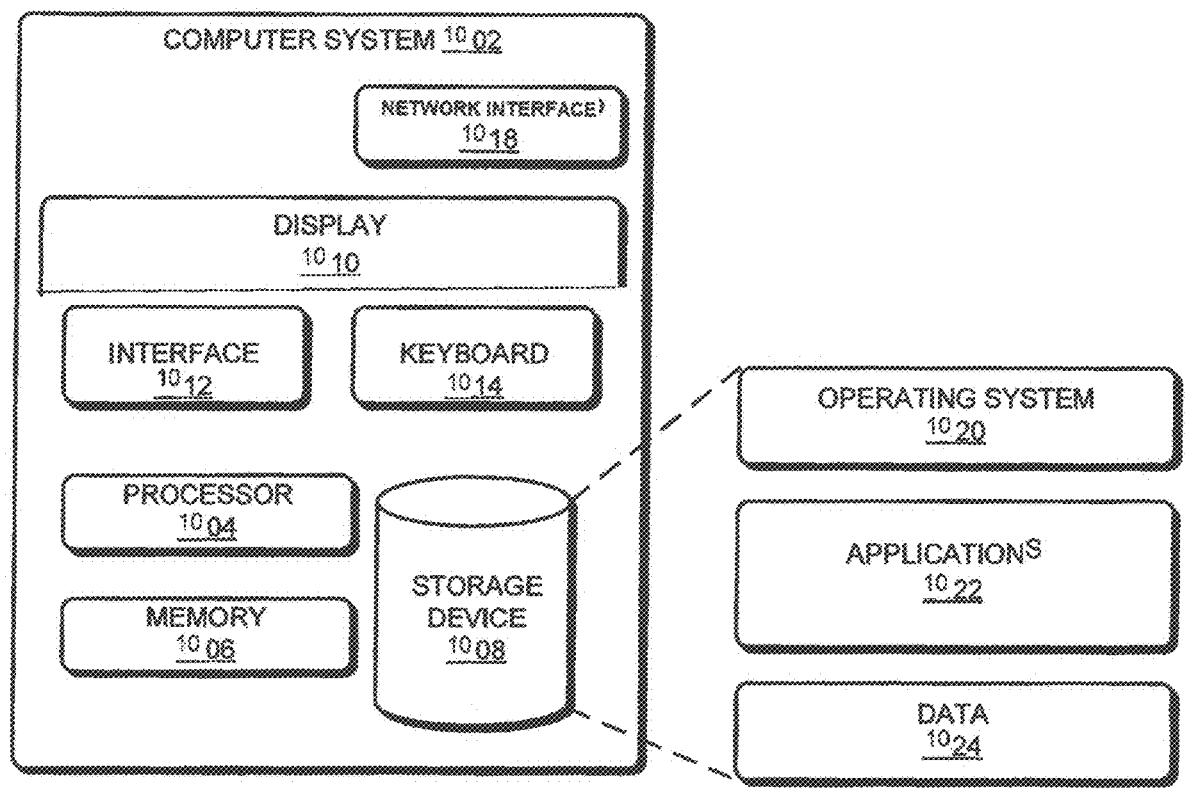
FIG. 10 depicts a computer platform for management of medical devices according to some embodiments.

FIG. 10 illustrates one embodiment of a computer system (e.g., a network server platform) 1002 that facilitates medical device management in accordance with some embodiments. Computer system 1002 includes processor 1004, memory 1006, storage device 1008, display 1010, interface components 1012, keyboard 1014. Computer system 1002 includes network interface 1018 for conducting network communications.

Memory 1006 can include a volatile and non-volatile memory. Storage device 1008 can store operating system 1020, device management applications 1022 for management of implantable devices and provision of remote medical care, and data 1024. Device management applications 1022 may include applications with software code to perform operations discussed herein including communication with patient controller devices, communication with clinician programmer devices validation of therapeutic data from clinician programming, analysis of programming data, auditing operations, distribution of revocation data, and any other appropriate device management operations.

Computer system 1002 may also store and access data through a cloud computing architecture with relevant data distributed across multiple platforms at different physical locations. Data 1024 can include any data relevant to patients, medical devices, physiological data, therapeutic settings, clinicians, and clinician devices for the management of medical devices, monitoring of patient status, detection of patient conditions, and any other task related to remote monitoring and management of health care for patients with medical devices. Data 1024 may include any of the data discussed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described above can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Figure 11:
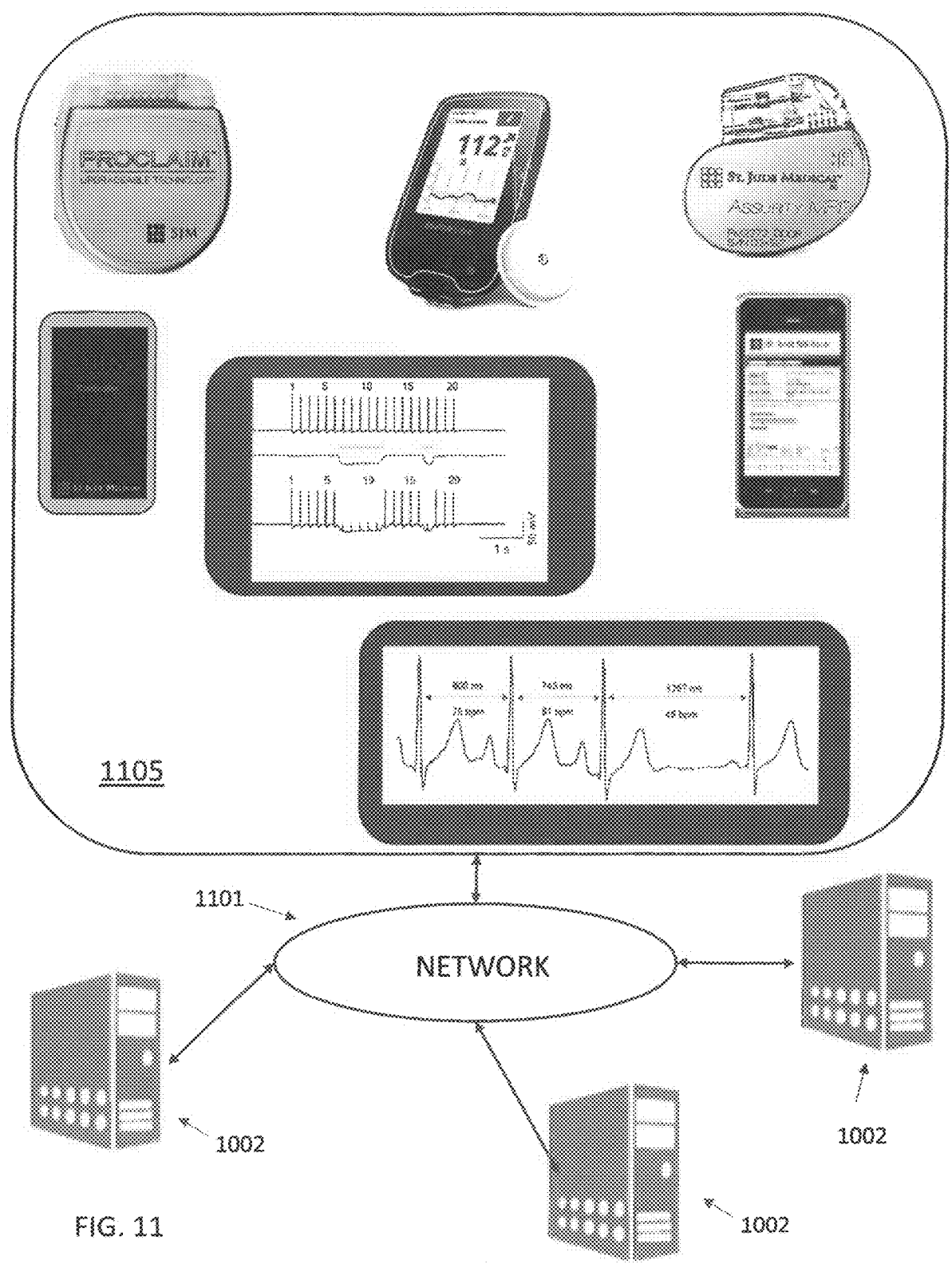
FIG. 11 depicts medical devices managed by a medical device management system according to some embodiments.

FIG. 11 depicts a collection of medical devices 1105 managed by a medical device management system according to some embodiments. The medical device management system includes a plurality of computer systems 1002 connected to network 1101 for management of devices 1105. The devices may include any number of devices and types of devices including neurostimulation devices, cardiac rhythm management devices, glucose monitoring devices, and medical agent infusion devices as examples. The devices may include the medical devices that provide the medical therapy and/or monitoring functionality, the patient controller devices, and clinician devices. The devices may monitor and communicate patient data for communication to one or more server platforms 1002. The patient data may include any relevant physiological data such as cardiac activity, respiration data, glucose levels, neurological activity, physical activity data, and/or the like. Communication of therapeutic settings, programming data, validation data, and revocation data between devices 1105 and one or more server platforms 1002 may occur as discussed herein.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. When processor-based, the controller executes program instructions stored in memory to perform the corresponding operations. Additionally or alternatively, the controllers and the controller device may represent circuits that may be implemented as hardware. The above examples are exemplary only and are thus not intended to limit in any way the definition and/or meaning of the term "controller."

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 45 U.S.C. § 112(f), unless and until such claim limitations expressly use the phrase "means for" followed by a statement of function void of further structure.

The invention claimed is:

1. A method of programming an implantable medical device (IMD) to provide therapeutic operations for a patient, comprising:
conducting a first communication session between the IMD with an external programming device;
receiving first programming data by the IMD from the external programming device to provide therapeutic operations according to at least one instance of settings data during the first communication session;
receiving, by the IMD, limitation data from the external programming device during one or more off-line programming sessions when a network connection to a remote programming device is unavailable, wherein the limitation data defines limitations on IMD operating parameters to restrict changes to therapeutic settings of the IMD during the one or more off-line programming sessions;
establishing, by the IMD, a second communication session with the external programming device when network connectivity between the remote programming device and the external programming device is not available;
receiving, by the IMD, second programming data from the external programming device to provide therapeutic operations according to at least one instance of settings data during the second communication session;
determining, by the IMD, whether the second programming data is permitted according to limitations defined by the limitation data; and
conducting, by the IMD, therapeutic operations according to the second programming data after determining that the second programming data is permitted by the limitation data.

2. The method of claim 1 wherein the limitation data identifies a range of the IMD operating parameters that are deemed safe for the patient.

3. The method of claim 2, wherein the IMD operating parameters comprise at least one of a range of pulse amplitude values and one or more electrode settings that should not be activated for therapeutic operations.

4. The method of claim 1 wherein the limitation data identifies one or more stimulation patterns that cause undesired neuronal synchronization or kindling in the patient.

5. The method of claim 1 wherein the limitation data identifies one or more cardiac resynchronization therapies.

6. The method of claim 1 wherein the limitation data identifies one or more cardiac therapy timing parameter limits.

7. The method of claim 1 wherein the limitation data identifies limits for provision of a pharmaceutic agent to the patient.

8. The method of claim 1 wherein the first communication session occurs while the external programming device has connectivity with the remote programming device and the first programming data and second programming data are validated with respective validation data cryptographically signed by the remote programming device and received with the first programming data and the second programming data.

9. The method of claim 1 wherein the limitation data is validated with validation data cryptographically signed with the external programming device.

10. The method of claim 1 wherein the second programming data is temporarily validated by validation data cryptographically signed with the external programming device that generated the second programming data.

11. An implantable medical device (IMD) comprising:
therapeutic circuitry for controlling delivery of a medical therapy to a patient;
a processor for controlling the IMD according to executable code;
wireless communication circuitry for conducting wireless communications; and
memory for storing data and executable code, wherein the executable code comprises code for causing the processor to:
conduct a first communication session with an external programming device;
receive first programming data from the external programming device to provide therapeutic operations according to at least one instance of settings data during the first communication session;
receive limitation data from the external programming device during one or more offline programming sessions when a network connection to a device management system is unavailable, wherein the limitation data defines limitations on IMD operating parameters to restrict changes to therapeutic settings of the IMD during the one or more offline programming sessions;
establish a second communication session with the external programming device when network connectivity between the device management system and the external programming device is not available;
receive second programming data from the external programming device to provide therapeutic operations according to at least one instance of settings data during the second communication session;
determine whether the second programming data is permitted according to limitations defined by the limitation data; and
conduct therapeutic operations according to the second programming data after determining that the second programming data is permitted by the limitation data.

12. The IMD of claim 11 wherein instances of therapeutic settings are validated with temporary validation data received during offline programming sessions.

13. The IMD of claim 12 wherein each instance of temporary programming data is signed with a cryptographic key corresponding to a clinician or clinician device.

14. The IMD of claim 11 wherein instances of therapeutic settings are validated with validation data signed with a cryptographical key corresponding to the IMD when the validation data is generated by the device management system.

15. The IMD of claim 11 wherein the memory of the IMD stores a collection of temporary keys and the processor searches the collection of temporary keys for a key that matches a temporary key used to sign validation data received during offline programming sessions.

16. The IMD of claim 11 wherein the IMD ceases communication sessions with clinician programming devices that attempt to utilize a cryptographic key that has been revoked.

17. The IMD of claim 11 wherein the executable code comprises code for causing the processor to:
  apply a checksum or digest function to at least data defining an instance of therapeutic settings; and
  use a cryptographical key for comparison against received validation data.

\* \* \* \* \*

UNITED STATES PATENT AND TRADEMARK OFFICE
CERTIFICATE OF CORRECTION

PATENT NO. : 11,173,313 B2  
APPLICATION NO. : 16/179753  
DATED : November 16, 2021  
INVENTOR(S) : Christopher S. L. Crawford Page 1 of 1

It is certified that error appears in the above-identified patent and that said Letters Patent is hereby corrected as shown below:

In the Specification

Column 1, Line 26, delete "dose" and replace with --close--.
Column 3, Line 48, delete "circuity" and replace with --circuitry--.
Column 3, Line 59, delete "IMO" and replace with --IMD--.
Column 6, Line 29, delete "insights" and replace with --Insights--.
Column 7, Line 13, delete "resource, Access" and replace with --resource. Access--.
Column 7, Line 18, delete "(RCS)" and replace with --(RCIS)--.
Column 8, Line 26, delete "Identify" and replace with --identify--.
Column 8, Line 27, delete "conditions, Alerts" and replace with --conditions. Alerts--.
Column 8, Line 31, delete "Interact" and replace with --interact--.
Column 9, Line 57, delete "implantation, Wireless" and replace with --implantation. Wireless--.
Column 9, Line 64, delete "Memory 363" and replace with --Memory 353--.
Column 15, Line 28, delete "patients" and replace with --patient's--.
Column 15, Line 50, delete "puke" and replace with --pulse--.
Column 15, Line 52, delete "puke" and replace with --pulse--.
Column 15, Line 54, delete "puke" and replace with --pulse--.
Column 15, Line 58, delete "puke" and replace with --pulse--.
Column 15, Line 59, delete "puke generator 850, electrical pukes" and replace with --pulse generator 850, electrical pulses--.
Column 15, Line 60, delete "puke" and replace with --pulse--.
Column 17, Line 40, delete "puke" and replace with --pulse--.
Column 17, Line 47, delete "puke" and replace with --pulse--.
Column 17, Line 48, delete "puke" and replace with --pulse--.

Signed and Sealed this  
Eleventh Day of January, 2022

Drew Hirshfeld  
*Performing the Functions and Duties of the*  
*Under Secretary of Commerce for Intellectual Property and*  
*Director of the United States Patent and Trademark Office*